United States Patent [19]
Chang

[11] Patent Number: 6,162,485
[45] Date of Patent: Dec. 19, 2000

[54] FINGERPRINTING SYSTEM AND METHOD

[75] Inventor: John C. H. Chang, Naperville, Ill.

[73] Assignee: Wallace Computers Services, Inc., Hillside, Ill.

[21] Appl. No.: 09/073,959

[22] Filed: May 7, 1998

[51] Int. Cl.[7] .......................... A61B 5/103; B41M 5/165; B41M 5/155; B41M 5/136

[52] U.S. Cl. .............................. 427/1; 427/145; 427/150; 427/152; 427/208.4; 118/31.5; 428/355 RA; 428/402.2; 428/914; 503/201; 503/206; 503/226

[58] Field of Search ............................... 427/1, 145, 150, 427/152, 208.4; 118/31.5; 428/914, 343, 355 R, 355 RA, 402.2; 503/200, 201, 206, 226

[56] References Cited

U.S. PATENT DOCUMENTS

| | | |
|---|---|---|
| 1,459,634 | 6/1923 | Miller . |
| 1,499,995 | 7/1924 | Merritt . |
| 1,746,955 | 2/1930 | Messer . |
| 1,810,493 | 6/1931 | Messer . |
| 2,153,684 | 4/1939 | Ballard .......................................... 41/4 |
| 2,500,612 | 3/1950 | Krogh ............................................ 41/4 |
| 2,929,736 | 3/1960 | Miller et al. ............................... 117/36 |
| 3,318,282 | 5/1967 | Bean ............................................ 118/9 |
| 3,318,428 | 5/1967 | Klein ........................................... 194/2 |
| 3,419,287 | 12/1968 | Rudie .......................................... 283/7 |
| 3,709,524 | 1/1973 | McKee et al. ......................... 282/22 R |
| 3,821,010 | 6/1974 | Vincent ................................... 117/36.2 |
| 3,831,552 | 8/1974 | Schmidt et al. ........................ 118/31.5 |
| 3,867,164 | 2/1975 | Orlando et al. . |
| 3,897,749 | 8/1975 | May et al. ............................... 118/31.5 |
| 3,954,803 | 5/1976 | Vincent et al. ........................... 260/335 |
| 3,971,335 | 7/1976 | Curtis et al. ................................. 118/6 |
| 4,010,292 | 3/1977 | Shackle et al. .......................... 427/150 |
| 4,029,012 | 6/1977 | Smith, III et al. ....................... 101/368 |
| 4,104,437 | 8/1978 | Vincent et al. .......................... 428/307 |
| 4,170,483 | 10/1979 | Shackle et al. ............................ 106/21 |
| 4,182,261 | 1/1980 | Smith, III et al. ..................... 118/31.5 |
| 4,317,743 | 3/1982 | Chang ...................................... 252/316 |

(List continued on next page.)

OTHER PUBLICATIONS

Brochure entitled "IdentaPrint—Security Identification System", IdentaPrint, Garland, Texas, Published prior to May 7, 1998.

*Primary Examiner*—Michael W. Ball
*Assistant Examiner*—Michael A Tolin
*Attorney, Agent, or Firm*—Roylance, Abrams, Berdo & Goodman, L.L.P.

[57] ABSTRACT

A system for forming fingerprints comprises a substrate bearing a designated print image-forming area and a localized coating of pressure-sensitive microcapsules containing a substantially colorless, image-forming reactant in the form of a color former or color-developer for forming a latent or visible image of a fingerprint in the designated print image-forming area. An image-developing device comprising a transparent film coated with a dual-functional adhesive composition comprising a pressure-sensitive adhesive containing an image-forming co-reactant in the form of a color developer or color former is used to form a protected visible image in the designated print image-forming area when applied to the fingerprint image.

12 Claims, 4 Drawing Sheets

U.S. PATENT DOCUMENTS

| | | | |
|---|---|---|---|
| 4,379,178 | 4/1983 | Meadows et al. | 427/1 |
| 4,425,386 | 1/1984 | Chang | 427/256 |
| 4,448,445 | 5/1984 | Chang et al. | 346/206 |
| 4,650,219 | 3/1987 | Sigman | 283/70 |
| 4,699,077 | 10/1987 | Meadows et al. | 118/31.5 |
| 4,702,194 | 10/1987 | Martin et al. | 118/31.5 |
| 4,705,299 | 11/1987 | Hedgcoth et al. | 283/68 |
| 4,706,600 | 11/1987 | Mason, Jr. et al. | 118/31.5 |
| 4,721,628 | 1/1988 | Pieper | 427/1 |
| 4,903,991 | 2/1990 | Wright | 283/95 |
| 4,917,987 | 4/1990 | Arndt et al. | 430/139 |
| 4,943,089 | 7/1990 | Reardon | 283/81 |
| 4,983,415 | 1/1991 | Arndt et al. | 427/1 |
| 5,009,919 | 4/1991 | Vassiliades | 427/1 |
| 5,013,071 | 5/1991 | Tremaine | 283/69 |
| 5,067,749 | 11/1991 | Land | 283/117 |
| 5,071,168 | 12/1991 | Shamos | 283/117 |
| 5,114,188 | 5/1992 | Koch | 283/68 |
| 5,160,171 | 11/1992 | Gregory et al. | 283/91 |
| 5,193,855 | 3/1993 | Shamos | 283/117 |
| 5,194,289 | 3/1993 | Butland | 427/1 |
| 5,283,152 | 2/1994 | Feldman et al. | 503/226 |
| 5,330,231 | 7/1994 | Godfrey | 283/78 |
| 5,395,444 | 3/1995 | Arndt et al. | 118/31.5 |
| 5,454,600 | 10/1995 | Floyd | 283/78 |
| 5,462,597 | 10/1995 | Jubran | 118/31.5 |
| 5,612,168 | 3/1997 | Ishikawa | 503/226 |
| 5,709,746 | 1/1998 | Ballard | 118/31.5 |
| 5,811,366 | 9/1998 | Chikami | 503/201 |
| 5,830,823 | 11/1998 | Vaughn et al. | 503/201 |

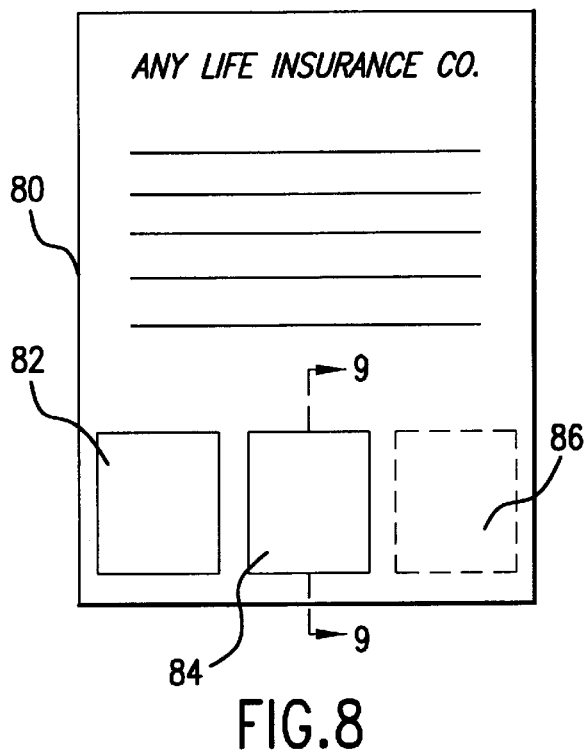
FIG.8
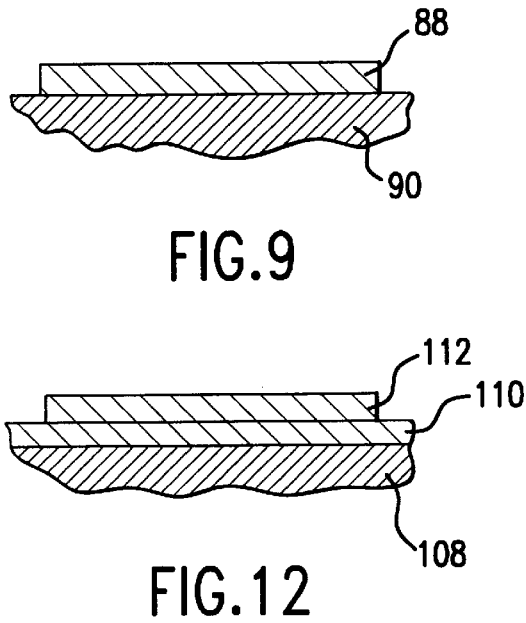
FIG.9
FIG.12
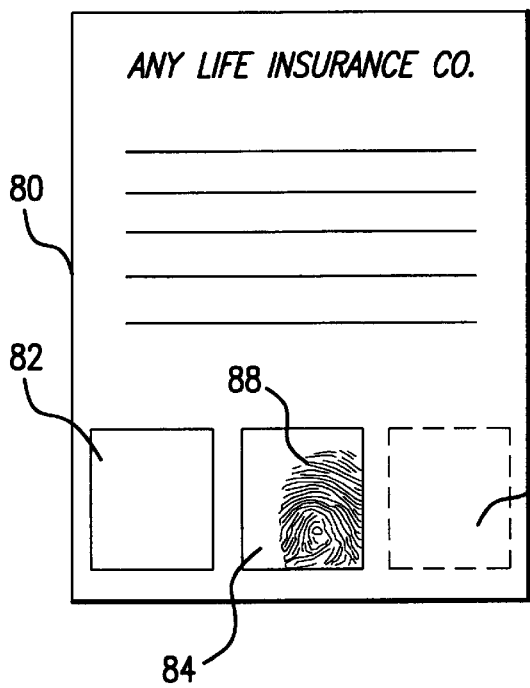
FIG.10
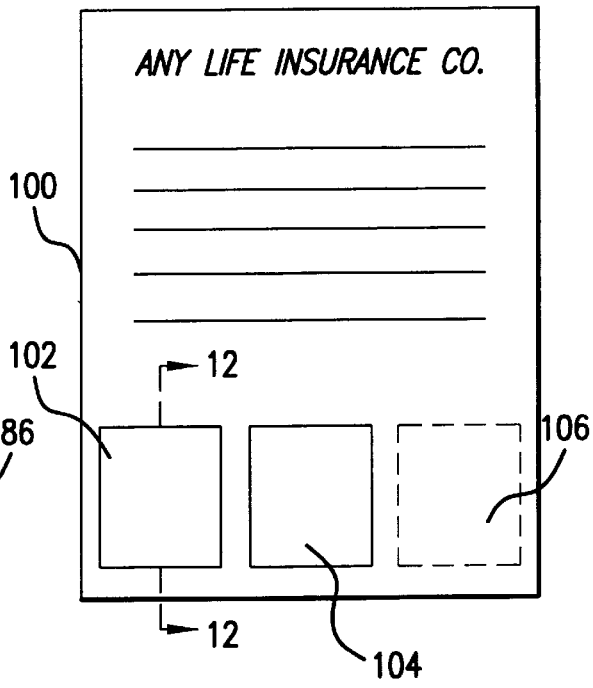
FIG.11

FINGERPRINTING SYSTEM AND METHOD

FIELD OF THE INVENTION

The present invention relates to a fingerprinting system for security documents and the method of using such security documents. More particularly, this invention relates to self-provided security documents having both a latent print image-providing medium, a print-image developing/protecting device used to form a visible print image on the document, and to a reactive adhesive composition for use in such device.

BACKGROUND OF THE INVENTION

The art of fingerprinting and identifying persons by their fingerprints is well known. The use of fingerprints for identification purposes is based upon distinctive ridge outlines which appear on the bulbs on the inside of the end joints of the fingers and thumbs. These ridges have definite contours and appear in several general pattern types, each with general and specific variations of the pattern, dependent on the shape and relationship of the ridges. A fingerprint can be classified according to its pattern type and this data can be systematically searched.

With the increasing fraud in many businesses of modern life, such as banking, rental, insurance, credit application, employment application and clinical laboratories, fingerprinting systems become an effective means of reducing unlawful activities by identifying the individual involved. Even to a lesser extent, it can deter potential law breakers who might have existing arrest records with the law enforcement authorities.

For example, clinical laboratories have problems with "stand-ins" who take the place of an individual to provide specimens in order to satisfy requirements for illegal substances testing. If there are suspicious circumstances surrounding the death of an insurance policy holder, the insurance company may obtain fingerprint copies of the deceased for comparison with their application record prior to paying out on the death benefit. When establishing a bank account, taking out a loan, or cashing a check, one might be asked for fingerprint authentication because the criminal might do it in one's name. Thus, the fingerprint system can protect honest citizens as well as work to convict or deter the criminals.

U.S. Pat. No. 3,867,164 to Orlando et al. discloses a fingerprint imprinting device which comprises three layers: the first layer is a thin conformable film coated with a wet ink on the surface facing the second layer, the second layer is a frame member having a window and the third layer is the print receiving surface. When a print is to be taken, the finger is pressed against the upper surface of the first layer to move its inked surface into contact with the designated print receiving area on the third layer. This device produces a print of identification character without getting the ink on the finger utilized to make the impression. However, the first layer, a thin film, which is opaque because of the wet ink must be removed to display the fingerprint.

U.S. Pat. No. 3,971,335 to Curtis et al. reveals a fingerprint inking apparatus which has a self-contained supply of ink and a drive means that automatically produces an uniform film of ink of the correct thickness on a thin elastic membrane which is supported on a compressible foam structure or between two rollers. A designated finger presses the inked surface of the membrane downward causing the membrane to conform around the finger, thereby transferring the ink to the finger. Fingerprint is obtained when the finger is rolled in a conventional manner on a fingerprint card. The elastic membrane stays on the structure or two rollers. Nevertheless, the user's fingers are soiled after fingerprinting.

U.S. Pat. No. 4,029,012 to Smith et al. reveals an ink stamp-like applicator for depositing fingerprints directly on a document. The applicator has a stamp housing of a pair of reservoirs with semi-sealed pads. One pad contains a liquid developer solution while the other pad contains a liquid reagent solution capable of reacting with the developer to deposit an insoluble colorant precipitate. The applicator applies the two reagents in the reservoirs onto two designated areas of the document. By pressing a finger over one area to transfer one reagent onto the finger and then apply it over the area of another reagent, the ridge pattern of a fingerprint is immediately developed. This invention requires an ink stamp-like applicator.

U.S. Pat. No. 4,705,299 to Hedgcoth discloses a plastic card which has an ink absorbent coating over a pre-assigned space on the card. The coating contains a chemical reagent capable of reacting with a substantially colorless developer solution in a pad applied by a finger to provide a perceivable colorant fingerprint ridge pattern. If desired, a thin film laminate or overlay of a clear permanent coating (e.g., an acetate) may be applied over the print for protection. A pad is needed.

U.S. Pat. No. 4,706,600 to Mason, Jr. et al. reveals a fingerprinting device having three components: (a) an ink kit box, (b) a record sheet, and (c) transfer strips. In component (a), there are dry ink, a plate, and an applicator. The applicator is used to rub the dry ink on a finger. Component (b) is a clear plastic. Component (c) consists of a protective cover (ply 1, a paper), a middle sheet (ply 2, a clear plastic), and a backing sheet (ply 3, a clear plastic). These three plies are adhered together by pressure-sensitive adhesive having differential adhesion. In use, the protective cover is removed so that the dry ink applied on the ridge pattern of a finger may be transferred onto the adhesive coated on the top side of ply 2. Plies 2 and 3 (still adhered together as one unit) are flipped and pressed against the record sheet which is component (c). The backing sheet is then peeled off, leaving the fingerprint sandwiched between two clear plastic sheets. Detached items are used in this system.

U.S. Pat. No. 4,943,089 to Reardon reveals a fingerprint sensitive pad which includes a protective cover, an imprinting material and a base sheet. The protective cover is a flexible transparent plastic, mylar or cellophane. The imprinting material is a transparent or semi-transparent substance, which has an adhesive-like coating on the surface facing the protective cover to receive the fingerprint image when a finger is pressed upon it. The fingerprinting consists of a pattern left by the oil from the finger on the substrate sheet. The adhesive-like coating on this surface serves primarily only to prevent finger movement and smudging as well as holding the flexible protective cover in place. This fingerprint sensitive pad is affixed to a document by an adhesive coated on the bottom surface of the imprinting material. The bottom surface may be made reflective before the adhesive coating. The reflective coating may be incorporated directly onto an area of the document reserved for the fingerprint. The fingerprints are not in any color or black color.

U.S. Pat. No. 5,009,919 to Vassiliades discloses a fingerprinting system which comprises an ink pad and a substrate for receiving fingerprints. The pad is capable of releasing an oil solution of a color former. The substrate is locally coated with a color developer in the area where fingerprint is to be imprinted. In use, a finger is pressed onto the fingerprinting pad and then pressed onto the coated substrate. A colored image immediately developed from the reaction between the color former and the color developer. An ink pad is required for this fingerprinting system.

U.S. Pat. No. 5,013,071 to Tremaine discloses a fingerprinting system utilizing a conventional fingerprint card, a fingerprint card holder, primary sheet, secondary sheet, and an ink pad. The fingerprint card is to receive fingerprint impressions for specific fingers. The fingerprint card holder keeps the card in place during imprinting. The primary sheet is a sandwich-like structure having a layer of adhesive between a front release liner and a rear release liner. The secondary sheet is a structure having a front transparent sheet and a rear release liner with a transparent layer of adhesive between them. An ink pad is needed to ink the designated finger. In use, the rear release liner of the primary sheet is removed so that the adhesive layer (together with the front release liner) is pressed over the designated area of the fingerprint card. The card is inserted into the holder. The front release liner of the primary sheet is removed to expose the adhesive layer and an inked finger is pressed over the adhesive layer to imprint the ridge pattern of the finger. The transparent sheet with the adhesive of the secondary sheet is peeled off and placed over the fingerprint to make it smear proof. An ink pad and detached items are needed for this invention.

U.S. Pat. No. 5,067,749 to Land reveals a fingerprinting system which has an adhesive coated transparent plastic tape to receive fingerprint. The tape is then turned over and disposed over a transparent print card. It may be necessary to coat the digits of an individual with a visible medium, such as powder or ink.

U.S. Pat. No. 5,114,188 to Koch discloses a fingerprinting device which is initially affixed on the extension tab of a security document. The device assembly has a protective strip covering a window which is situated on a layer of adhesive coated on a transparent plastic material. The underside of the protective strip is coated with a release material, such as silicone or wax. The strip is to keep the adhesive from drying and to prevent the adhesive from collecting foreign matter. The adhesive is to receive the imprinting. The transparent plastic material is glued or attached to the tab. The fingerprint is recorded by pressing a finger on a layer of adhesive which is coated on a transparent plastic material. The device assembly still glued or attached to the tab is broken away from the security document and is kept in a storage tray. The print is developed by making a copy of it on a sensitized surface by back radiant energy, such as a photocopy machine, through the adhesive, the transparent plastic material and then the tab. The subject's fingers are not dirtied or exposed to chemicals.

SUMMARY OF THE INVENTION

An imprinting system for forming fingerprints has now been found, which comprises a first substrate having a first surface bearing a designated print image-forming area, the first substrate further bearing a localized coating of pressure-sensitive microcapsules containing a substantially colorless color former(chromogen) or color-developer for forming an image of a fingerprint in the print image-forming area. The localized coating of pressure-sensitive microcapsules is spaced apart from the designated print image-forming area. Preferably, the present printing system is self-provided, so that in such embodiment the first substrate also bears an image-developing device comprising a second substrate that is substantially transparent and has a first surface and a second surface. The first surface of the second substrate is coated with a dual-functional, reactive adhesive composition comprising a pressure-sensitive adhesive and a color developer or color former capable of reacting with the microencapsulated color former or color developer, respectively, to form a visible, colored image in the designated print image-forming area. The second substrate is releasably attached to the first substrate and spaced apart from both the designated print image-forming area and the localized coating of the pressure-sensitive microcapsules.

The expression "substantially transparent" as used in the present application in reference to the substrate or film means that the substrate, member or film is sufficiently transparent or translucent that an underlying visible fingerprint image can be viewed through the substrate or film by the unaided or naked eye.

Since color formers and color developers constitute reaction pairs, it will be understood that whenever the term "color former" is used in the present application, a "color developer" could be substituted and vice versa, so long as a reaction pair is used. However, for purposes of illustration, the encapsulated reactant will be referred to as a color former and the unencapsulated co-reactant will be referred to as a color developer.

Likewise, the term "fingerprinting" as used herein will be understood to include reproduction of a visible print image of the distinctive ridge outlines of the end joints of any digit of a human limb, including fingers, thumbs or toes.

The designated digit to be printed, such as an index finger or a toe, is applied to the localized coating of the pressure-rupturable microcapsules under sufficient pressure to rupture the microcapsules, release the color former from the microcapsules and coat the color former on the designated member including the distinctive ridge pattern to be printed. Next, the designated member is applied to the print image-forming area to transfer the color former in the form of the distinctive ridge pattern to the print image-forming area to thereby form a latent image of the print of the ridge pattern in the print-image forming area.

The transparent substrate bearing the reactive adhesive is separated or peeled from said first substrate and placed over the print-image forming area with the reactive pressure sensitive adhesive in direct contact with the latent image in the print-image forming area. A colored visible image of the distinctive ridge pattern is immediately formed by reaction of the color developer in the pressure-sensitive adhesive with the color former. The visible image is permanently protected by the transparent member which is adhered to the print-image forming area by the reactive adhesive.

The document system of the present invention is preferably a "self-provided" fingerprinting document system in which all necessary print-image forming reactants and co-reactants are supplied directly on the security document. Unlike prior systems, the present system of the present invention is self-provided and does not require a conventional ink pad, mechanical support or other detached items. An important advantage of using an integral, image-forming localized coating or "patch" in the form of substantially colorless, pressure-rupturable microcapsules containing color former is to provide a controlled amount of color-former for forming the print image. In addition, the user's fingers are not stained during the fingerprinting operation. More importantly, the present invention provides a simple, defacement-proof fingerprinting system with a readily available supply of color former and color developer on the security document.

According to one embodiment of the present invention, the designated print image-forming area is substantially free from material capable of reacting with the encapsulated color former to form a visible image prior to application of the print image in the form of the color former. In this embodiment of the present invention, application of the color former to the print image-forming area from the designated member forms a latent image of the ridge pattern of the designated member. Subsequent application of the image developing device comprising the transparent substrate bearing the reactive adhesive to the latent image forms a colored visible image when the color former reacts with the color developer in the reactive adhesive.

According to a further embodiment of the invention, the image-forming area is initially coated with a color developer, so that application of the color former from the designated member to the pre-coated print image-forming area immediately forms a visible print image of the ridge pattern of the designated digit in the print image-forming area. Subsequent application of the image-developing device, which comprises the transparent substrate bearing the reactive adhesive, to the latent image is optional. However, use of the image-developing device in this manner results in a more intense colored visible image protected by the adhered transparent substrate.

According to another embodiment of the present invention, a reactive adhesive is provided, which comprises a pressure-sensitive adhesive having incorporated therein a color developer or color former that will react with to form a visible, colored image when contacting a color former or color developer, respectively.

Another embodiment of the present invention comprises a dual-functional image-developing device, which comprises a substantially transparent substrate bearing a reactive adhesive, which comprises a pressure-sensitive adhesive having incorporated therein a color former or a color developer capable of reacting with a color developer or color former, respectively, to form a visible, colored image.

Although the dual-functional image-developing device is preferably located on the same document as the microcapsular image-forming patch, the dual-functional image-developing device may be located on a separate substrate. Thus, another embodiment of the present invention comprises an imprinting kit for forming fingerprints which comprises a first substrate, and a second substrate capable of being closely associated with the first substrate. The first substrate has a first surface bearing a designated print image-forming area and a localized coating of pressure-sensitive microcapsules containing a substantially colorless, color former for forming an image of a print in the localized, print image-forming area. The localized coating of pressure-sensitive microcapsules is spaced apart from the designated print image-forming area.

The second substrate is substantially transparent and has a surface coated with a dual-functional, reactive adhesive composition comprising a pressure-sensitive adhesive and a color developer. In this embodiment of the invention, the image-developing device is releasably attached to a third substrate and can be removed from the third substrate and placed over the designated print image-forming area after a print image is imparted to the designated print image-forming area. The substantially transparent second substrate is adhered to the designated print image-forming area by means of the dual-functional reactive adhesive composition such the color developer contained in the adhesive composition can react with the color former forming the print image.

BRIEF DESCRIPTION OF THE DRAWINGS

Referring now to the drawings which form a part of the original disclosure:

FIG. 8 is a front view of a security document in the form of a life insurance application using a different embodiment of the invention for receiving a fingerprint;

FIG. 9 is an enlarged, diagrammatic cross-sectional view taken on line 9—9 of FIG. 8 showing a modified print-forming area of the security document;

FIG. 10 is a schematic view of the security document of FIG. 8 showing development of fingerprint without formation of a latent image;

FIG. 11 is a front view of a security document in the form of a life insurance application employing a further embodiment of the invention for providing a fingerprint;

FIG. 12 is an enlarged, diagrammatic cross-sectional view taken along line 12—12 of FIG. 11 showing the microcapsular patch on a substrate fully coated with a co-reactant;

DETAILED DESCRIPTION OF THE INVENTION

Figure 1:
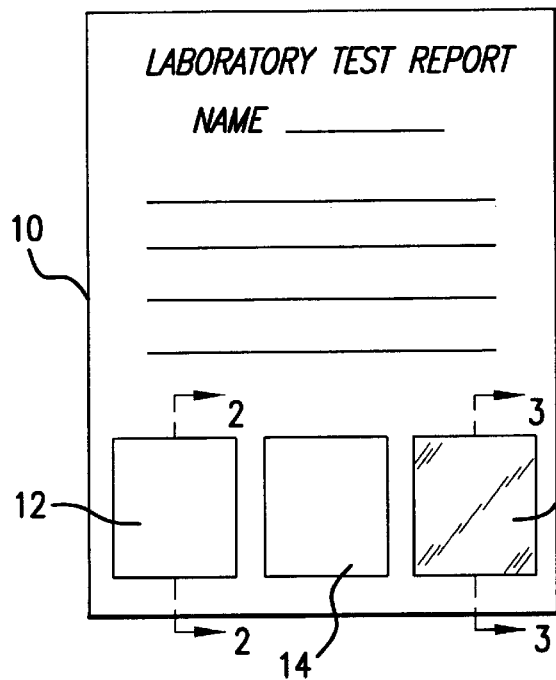
FIG. 1 is a front elevational view of a security document in the form of a laboratory test report for receiving a fingerprint in accordance with the present invention.

Referring to the drawings, FIG. 1 illustrates a security system in combination with document 10.

In the embodiment of FIG. 1, document 10 is a laboratory test report having a localized or spot-coating of pressure-rupturable microcapsules containing a substantially colorless color-former in area 12. A designated print image-forming area 14, where fingerprints are to be imprinted for identification or authentication purposes, is provided on document 10. Area 14 is free of color-former or color developer.

Figure 2:
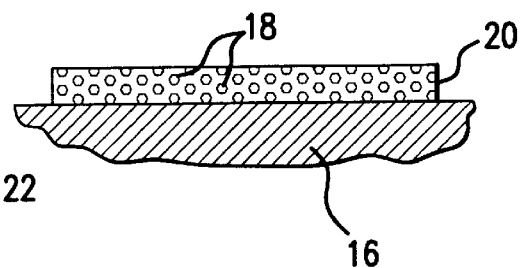
FIG. 2 is an enlarged, diagrammatic cross-sectional view taken on line 2—2 of FIG. 1 showing the microcapsular "patch" of the security document.

As seen in FIG. 2, paper substrate 16 is provided with coating 20 containing pressure-rupturable microcapsules 18 containing a substantially colorless, color former, which, as previously explained, may be either a color former (chromogen), or a color developer, but for simplicity, will be referred to as a color former.

Any suitable color former or color developer useful for forming visible colored images may be used in the present invention. For example, color formers and color-developers conventionally used in pressure-sensitive copying systems are the preferred reactants and co-reactants in this invention. Either color formers or color developers can be encapsulated or incorporated in the pressure sensitive adhesive, as desired. However, it is generally preferred to produce the latent image from a chromogenic compound, so that color formers are preferably encapsulated and color developers are preferably incorporated in the pressure-sensitive adhesive.

The color former is substantially colorless before reacting with the substantially colorless color developer to produce the visible colored image. Suitable color formers include, for example, diarylmethanes, triarylmethanes, indolylphthalides, azaphthalides, fluorans, and spiropyrans. Exemplary diarylmethanes include 4,4'-bis(dimethylaminobenzhydrylbenzyl)ether, N-halophenyl leuco auramine, and N-2,4,5-trichlorophenyl leuco auramine. Examples of triarylmethanes include 3,3-bis(p-dimethylaminophenyl)-6-dimethylaminophthalide and 3,3-bis(p-dimethylaminophenyl)phthalide. Examples of indolylphthalides include 3-(p-dimethylaminophenyl)-3-(1,2-dimethylindole-3-yl)phthalide, 3,3-bis(1-octyl-2-methylindol-3-yl)phthalide and 3-(p-dimethylaminophenyl)-3-(2-methylindole-3-yl)phthalide. Examples of azaphthalides include 3-(2-ethoxy-4-diethylaminophenyl)-3-(1-octyl-2-methylindole-3-yl)-4-azaphthalide and 3-(2-ethoxy-4-diethylaminophenyl)-3-(1-ethyl-2-methylindole-3-yl)-4-azaphthalide. Examples of fluorans include 2-dibenzylamino-6-diethylamino 2-anilino-6-diethylaminofluoran, 3-methyl-2-anilino-6-diethylaminofluoran, 2-anilino-3-methyl-6-(ethyl-isopentylamino)fluoran, 2-anilino-3-methyl-6-dibutylaminofluoran, 2-chloro-3-methyl-6-diethylaminofluoran, 3,6-dimethoxyfluoran, and 7,7'-bis(3-diethylaminofluoran). Examples of spiropyrans include 3-methylspirodinaphthopyran, 3-ethylspirodinaphthopyran, 3,3'-dichlorospirodinaphthopyran, 3-benzylspirodinaphthopyran, and 3-methylnaphtho-(3-methoxybenzo)spiropyran. Other suitable chromogenic compounds are disclosed in U.S. Pat. Nos. 3,821,010; 3,954,803; and 4,104,437 to Vincent and Chang, the entire disclosures of which are hereby incorporated by reference.

The color former utilized to form the latent image may be dissolved in a solvent, such as benzyl xylenes, diaryl alkanes, monobutylbiphenyls, monoisopropylbiphenyls, dibutylbiphenyls, di-isopropylbiphenyls, monoisopropylnaphthalenes, di-isopropylnaphthalenes, and hydrogenated terphenyls.

Color developers useful in pressure-sensitive copying systems are the preferred color developers for the color formers of the present invention. Suitable color developers for incorporation into the pressure sensitive adhesive include, for example electron-acceptor materials, such as Lewis acids. Preferred electron-acceptor materials for inclusion in chromogenic composition 22 are the Lewis acids conventionally used to prepare carbonless copy papers. Preferred Lewis acids include, for example, zincated alkylphenol-formaldehyde novolac resins, zinc salts of alkylsalicylic acids, polymeric zinc salycilates, and the like.

By rubbing the ridge pattern of a designated finger over area 12, the pressure-rupturable microcapsules are ruptured and release the color former, which coats the ridge pattern of the finger. The designated finger bearing the color former is then pressed onto area 14 to transfer the color former and form a latent image of the fingerprint ridge pattern in designated print image-forming area 14.

In this manner, microcapsular area 12 serves as a "latent ink patch" and is able to provide controlled quantities of color former to the designated finger.

In order to transfer an adequate amount of reactant onto the finger, microcapsules may have an average particle diameter of from about 5 microns to about 50 microns, preferably from about 10 microns to about 25 microns. Although the larger capsules can supply ample amounts of reactant to the finger, larger capsules are more susceptible to damage during coating and normal handling processes.

Microcapsular area 12 may be anywhere on either the front or rear of the security document. As depicted in FIG. 1, the microcapsules are spot-coated on area 12 of security document 10, in the vicinity of area 14. For convenience, it is preferred to have the microcapsular "patch" 12 near or adjacent the designated print image-forming area 14.

Pressure-rupturable microcapsules useful in the present invention may be formed in any suitable manner conventionally employed. For example, capsules formed from coacervation of gelatin, polycondensation of urea-formaldehyde, interfacial cross-linking, or hydrolysis of isoclyanatoamidine products may be used. Preferably, the microcapsules are formed by a microencapsulation process described in U.S. Pat. No. 4,317,743 to Chang, the entire disclosure of which is hereby incorporated by reference.

A suitable binder material is needed to adhere the chromogen-containing pressure-rupturable microcapsules onto the surface of substrate 16. The amount of binder generally used is about 10 to about 50 percent by weight, and preferably about 15 to about 35 percent by weight, based on the total weight of the solids of the microcapsular coating composition. Examples of useful binders include starch, hydroxyethyl cellulose, methyl cellulose, carboxymethyl cellulose, gelatin, casein, gum arabic, polyvinyl alcohol, styrene-maleic anhydride copolymers, ethylene-acrylic acid copolymers, styrene-butadiene copolymers, acrylonitrile-butadiene copolymers, vinyl acetate emulsions, ethylene-vinyl acetate emulsions.

The microcapsular coating composition of the present invention may optionally additionally contain a color suppressant to prevent premature coloration. The color suppressant must be so chosen that it will not inhibit or adversely affect the color formation in the final product. Examples are ammonium hydroxide, alkanolamines, such as monoethanol amine, diethanolamine, N, N-dimethylethanolamine, and the like, condensates of amineformaldehyde, such as urea-formaldehyde, melamineformaldehyde, and the like. Suitable amounts of such color suppressants include from about 0.1 to about 10, preferably from about 0.5 to about 4 percent by weight based on the total dry weight of the coating composition. Other suitable color suppressants are disclosed, for example, in U.S. Pat. Nos. 4,010,292 and 4,170,483, the entire disclosures of which are hereby incorporated by reference.

The microcapsular coating composition may be applied to the substrate 16, which may be for example, paper, plastic, or the like, which forms the document, by any suitable technique known in the art to provide a localized, spot or band coating. In a preferred embodiment of the invention, the chromogenic coating composition is prepared as a slurry comprising the chromogen-containing pressure-rupturable microcapsules. A preferred method of coating is by off-set gravure coating as disclosed in U.S. Pat. No. B1 4,425,386 to Chang the entire disclosure of which is hereby incorporated by reference. Alternative preferred coating methods include flexographic, screen printing, nozzle extrusion and ink jet printing.

Figure 3A:
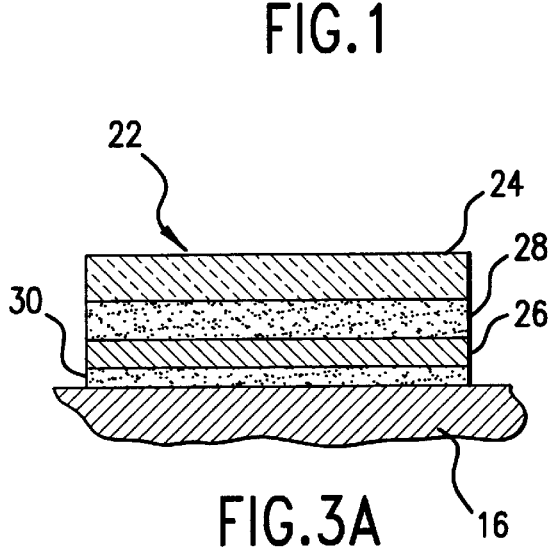
FIG. 3A is an enlarged, diagrammatic cross-sectional view taken on line 3—3 of FIG. 1 showing one form of attachment of the dual-functional, image-developing device to the security document.

Referring now to FIG. 3A, the latent image formed by the color former in area 14 is developed by use of an image-developing device 22, which is adhered to document 10 for subsequent use. As shown in FIG. 3A, image developing device 22 has a laminate construction comprising a plurality of layers in superposed relation. A patch of transparent film 24 is laminated with a release liner 26 by a reactive pressure-sensitive adhesive layer 28, which contains a substantially colorless color developer that will form a visible colored image when in contact with the latent image formed by the color former in area 14. Release liner 26 is adhered to substrate 16 of the security document on the non-release side of the release liner 26 by means of permanent laminating or non-pressure sensitive adhesive 30.

Figure 3B:
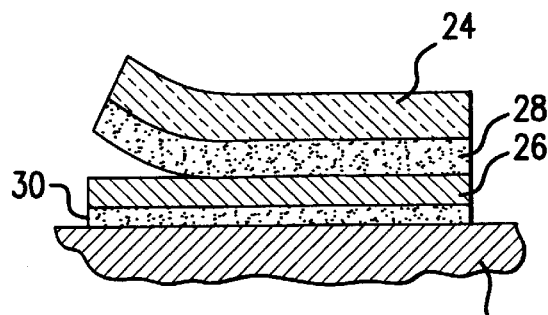
FIG. 3B is a view of FIG. 3A with separation of the transparent film and adhesive from the release sheet.

As seen in FIG. 3B, the transparent film 24 along with the reactive pressure-sensitive adhesive 28 can be easily peeled from release liner 26 for later application is to the latent image on area 14, when desired.

Figure 3C:
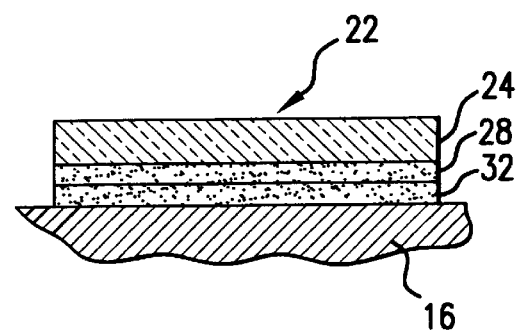
FIG. 3C is an enlarged, diagrammatic cross-sectional view taken on line 3—3 of FIG. 1 showing another form of attachment of the dual-functional, image-developing device to the security document.

Alternatively, as shown in FIG. 3C, the image-developing device 22 may be provided by coating the reactive pressure-sensitive adhesive 28 on a transparent film 24, which is then die-cut into the desired size and tagged onto a pre-determined area of substrate 16 of the security document which has been coated with a release material 32. This eliminates the need for a release liner on the security document and reduces the localized thickness, thereby making it easier to feed the security documents through printers in some cases. Release material 32 may be formed directly on document 10 by printing of silicone oil, a coating of a UV-curable silicone-containing polymer, a coating of hard petroleum-based wax, a coating of silicone-containing polymer, carbamates of polyvinyl alcohol, polyvinyl ethers of alkyl alcohol, or a printing of silicone wax.

Figure 4:
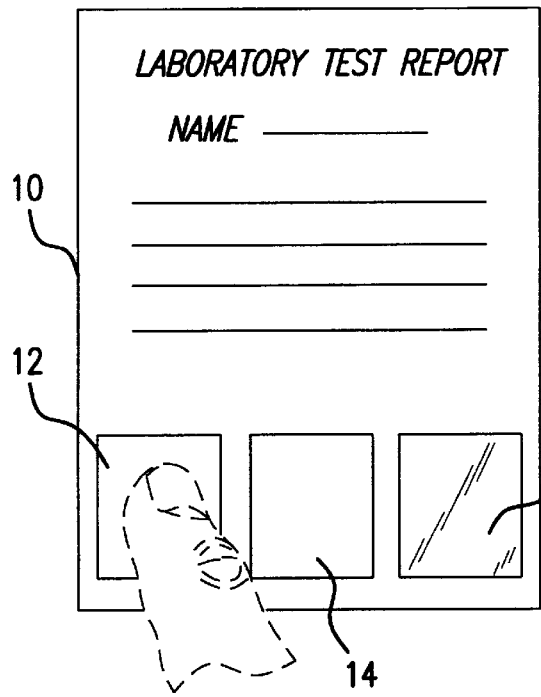
FIG. 4 is a schematic view of the security document of FIG. 1 showing use of the microcapsular patch.
Figure 5:
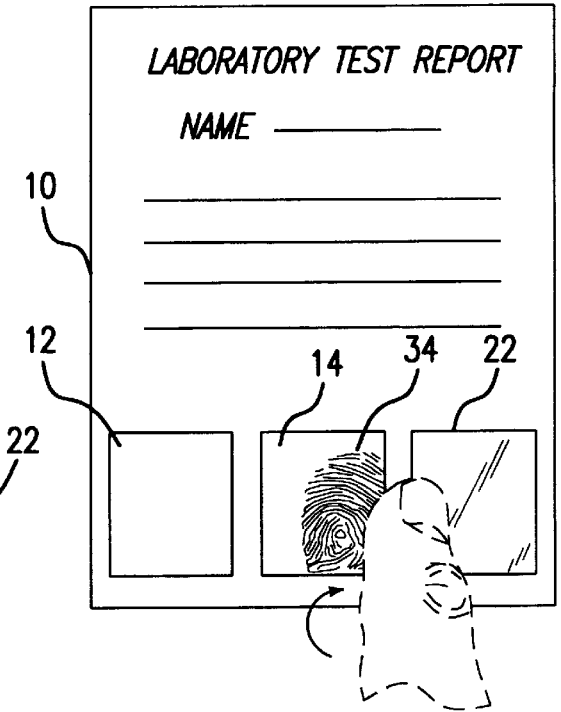
FIG. 5 is a schematic view of the security document of FIG. 1 showing formation of a latent print image.

Referring now to FIG. 4, use of the laboratory test sheet 10 of FIG. 1 for providing a permanent fingerprint record is illustrated. A selected digit, such as the forefinger of one hand, is applied to the microcapsular coating in area 12 with pressure, causing the microcapsules containing color former directly under the fingertip to rupture and release color former onto the fingertip. Next, the fingertip is applied with pressure to designated print-image forming area 14 to form latent image 34 of the ridge pattern fingerprint of the fingertip, and the fingertip is then withdrawn as depicted in FIG. 5.

Figure 6:
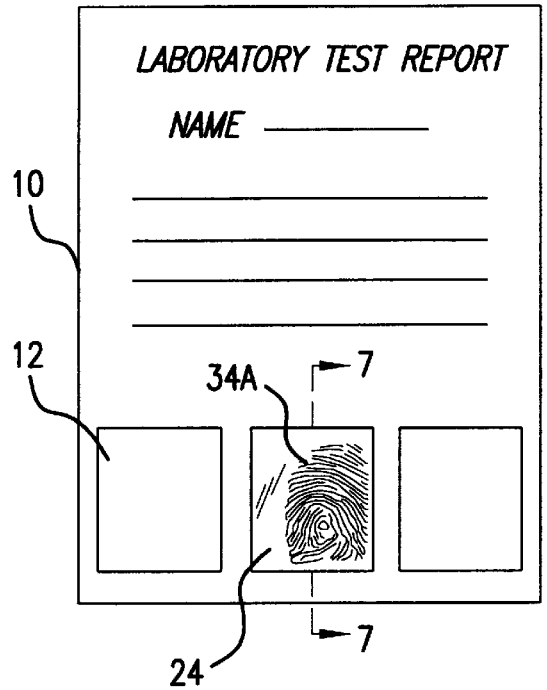
FIG. 6 is a schematic view of the security document of FIG. 1 showing the reattached image-developing device to develop the latent image.

Next, as depicted in FIG. 3B, the transparent film 24 together with reactive pressure-sensitive adhesive 28 of the image-developing device 22 are peeled away from release liner 26 and placed over latent print image 34 such that the reactive pressure-sensitive adhesive is superposed in direct contact with the latent image 34. The color developer in the pressure-sensitive adhesive instantly reacts with the color former in the latent image, as seen in FIG. 6, to form a visible colored image 34A of the colored fingerprint of the ridge pattern underneath transparent film 24.

Figure 7:
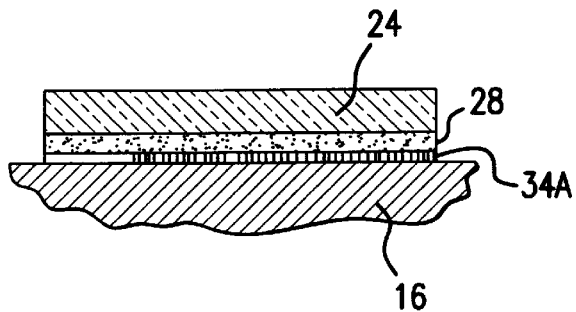
FIG. 7 is an enlarged, diagrammatic cross-sectional view taken on line 7—7 of FIG. 6 showing the dual-functional, image-developing device reattached to the security document.

As seen in FIG. 7, transparent film 24 and reactive pressure-sensitive layer 28 are directly over visible image 34A and serve to protect the fingerprint from being defaced. Reactive pressure-sensitive adhesive 28 serves a dual-performing purpose by supplying the color developer for conversion of the latent image of the ridge pattern into a visible image, and by adhering the transparent film to the fingerprint so that it will not be marred or defaced.

Reactive adhesive composition 28 is prepared by incorporating the color developer or color former into the pressure-sensitive adhesive prior to coating. Pressure-sensitive adhesives suitable for use in composition 28 of the present invention include, for example, polyisobutylene, styrene-isoprene-styrene block copolymers, styrene-butadiene rubber, natural rubber, styrene-butadiene rubber, ethylene-alphaolefin rubber, butyl rubber, polyurethane, polyisoprene-alkyldiacrylate copolymer, and ethylene vinyl acetate-based adhesives. The adhesives may be coated as aqueous, hot-melt or in solvent material. Suitable amounts include from about 1 to about 6 parts of pressure-sensitive adhesive per part by weight of color developer, preferably from about 1.7 to about 4 parts by weight of pressure-sensitive adhesive per part by weight of color developer. Likewise, if a color former is incorporated into reactive adhesive composition 28, suitable amounts include from about 5 to about 20 parts of pressure-sensitive adhesive per part by weight of color former, preferably from about 8 to about 15 parts by weight of pressure-sensitive adhesive per part by weight of color former.

Optionally, viscous polybutene may also be added to the pressure-sensitive adhesive to maintain the tacky nature of the finished product. Hydrophobic oil normally used in microencapsulation may be added to facilitate the dissolving of the color former or color developer in solvent-based and hot-melt type adhesives to increase the reactivity of the finished product.

Film 24 is substantially transparent, so that the fingerprint can be easily viewed through film 24. Suitable films may be made, for example from polyethylene, polypropylene, polyester, polystyrene, polyvinyl chloride, cellophane, and the like. Likewise, suitable films for use as film 24 are also described in U.S. Pat. No. 4,448,445 to Chang et al, the entire disclosure of which is hereby incorporated by reference.

The reactive pressure-sensitive adhesive is preferably coated on the release surface of a release liner followed by lamination with the transparent film so that the assembly may be die-cut and glued on the security document.

Release liner 26 may be any suitable form of release liner. For example, release liner 26 may be a paper substrate having a non-sticking surface on one side formed of silicone-containing polymers, petroleum-based waxes, carbamates of polyvinyl alcohol, or polyvinyl ethers of alkyl alcohol.

In the embodiments of FIGS. 1–7, designated print image-forming area 14 is free or substantially free of color formers until the designated finger transfers a color former to area 14 to form a latent image print of the ridge pattern. However, a further embodiment of the present invention is shown in FIG. 8.

Referring now to FIG. 8, life insurance form 80 is provided with area 82 coated with microcapsules containing color former in the same manner as area 12 of FIGS. 1 and 2. While designated print image-forming area 14 of FIG. 1 is uncoated, designated print image-forming area 84 is spot-coated with a color developer. As shown in FIG. 9, substrate 90 is provided with a spot coating 88 of a substantially colorless color developer. By rubbing the ridge pattern of a designated finger over area 82 to rupture the microcapsules to coat the ridge pattern of the finger with a color former and thereafter pressing the ridge pattern within area 84, an instant, visible colored fingerprint 88 of the ridge pattern develops in area 84, as shown in FIG. 10.

This technique, in which no image-developing device is provided in area 86, and therefore, no image-developing device is used, provides a quick fingerprinting approach for form 80 where organic solvents are not used in the surrounding area and long preservation of the fingerprint is not necessary. However, if desired, a transparent film with a reactive pressure-sensitive adhesive having the construction of FIG. 3A or 3C can be provided in area 86. Thereafter, the transparent film coated with the reactive adhesive and pressure-sensitive adhesive may be removed and applied to the developed fingerprint in area 84 with the reactive adhesive over and in contact with the fingerprint. The resultant fingerprint not only becomes more visible or darker by virtue of further reaction with the color developer in the adhesive with the color former, but, in addition, the fingerprint image is protected from marring by the transparent film.

Another embodiment of the present invention is illustrated in FIG. 11, in which form 100 has microcapsular area 102, print-image forming area 104 and optional developing device area 106, in a manner similar to the form of FIG. 8. However, substrate 108 of form 100 is fully coated with a color developer, such as a Lewis acid. Such papers having a coating of a color developer on the surface are commercially available from paper manufacturers. For example, smooth printing paper may have clay coated on the surface as the filler to provide quality printing. Likewise, paper for ink-jet printers may contain silica which can insolubilize the water-soluble ink-jet ink on the paper surface. Clay and silica are examples of well-known Lewis acids which react with color formers to provide visible images in pressure-sensitive copying system.

As seen in FIG. 12 microcapsular area 102 comprises substrate 108, which supports coating 110 of a color developer, such as clay or silica. Optionally, substrate 108 may be a substrate having a Lewis acid incorporated in the substrate, rather than having the substrate fully coated with a Lewis acid. For example, the substrate of the present invention may be a paper or plastic sheet having silica particles incorporated in the sheet. Thus, a sheet of TESLIN, which is a microporous polyolefin sheet filled with fine silica particles manufactured by PPG Industries, Inc., Barberton, Ohio, may be used as the substrate in the present invention. Coating 110 supports coating 112 comprising pressure-rupturable microcapsules containing a color former.

By rubbing the ridge pattern of a designated finger over area 102 to rupture the microcapsules, the color former is released and the ridge pattern of the finger is coated with the color former. Thereafter, the ridge pattern of the designated finger is imprinted within area 104, and an instant, visible colored fingerprint of the ridge pattern (not shown) develops in area 104, similar to print 88 in area 84 shown in FIG. 10.

When the designated finger is rubbed over area 102 to rupture the microcapsules and release the color former, a minor portion of the released color former reacts with the underlying color developer coating 110 to form a visible color of amorphous shape. If it is desired to prevent color formation in area 102, microcapsular coating 112 can be supplied by a die-cut rectangle of such microcapsular coating on uncoated paper, plastic or other substrate and glued to area 102. In this manner, the paper serves as a barrier layer to prevent contact between the encapsulated color-former and the color-developer coating 110 on substrate 108.

Likewise, the laminate of FIG. 12 can be formed with a barrier coating between layers 110 and 112, such as described in U.S. Pat. No. 2,929,736 to Miller et al., the entire disclosure of which is hereby incorporated by reference.

Figures 13, 14:
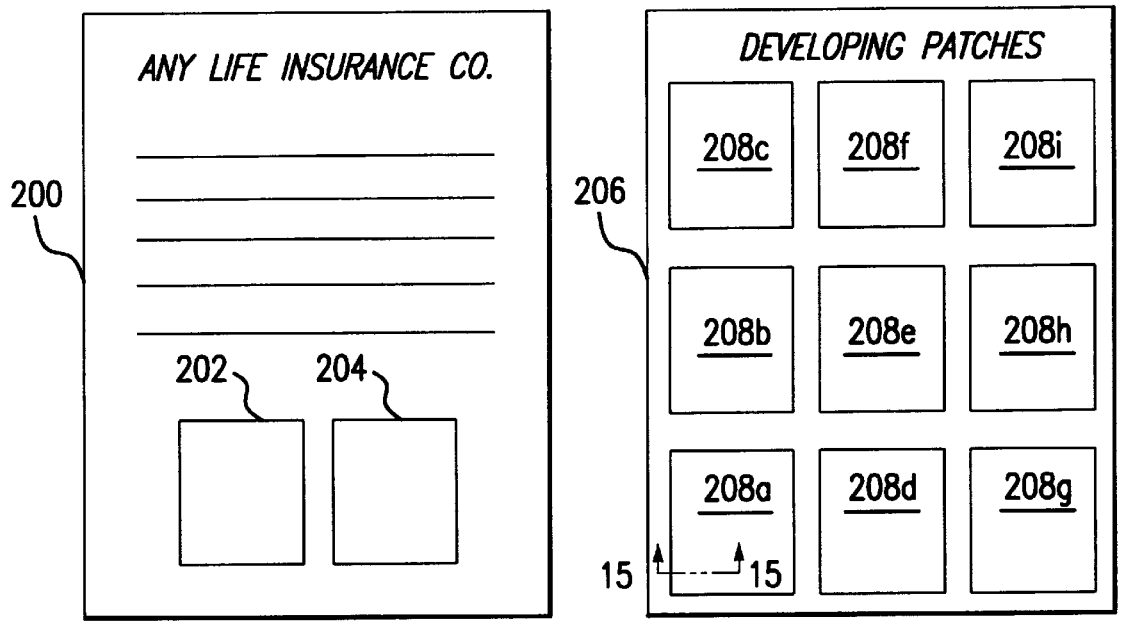
FIG. 13 is a front view of a security document in the form of a life insurance application used with an image-developing device on a separate substrate.
FIG. 14 is a front elevational view of a supply document for separately providing the image-developing device for use with the security document of FIG. 13.
Figure 15:
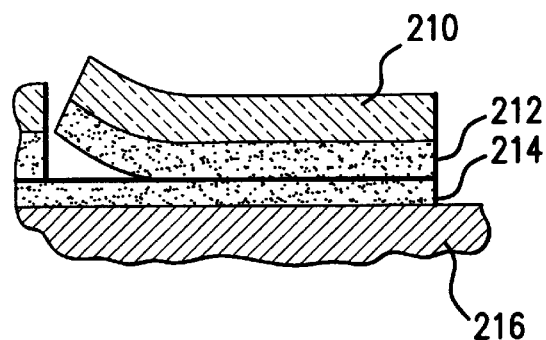
FIG. 15 is an enlarged, diagrammatic cross-sectional view taken along line 15—15 of FIG. 14 showing partial removal of an image developing device from the supply document.

Referring now to FIG. 13, an embodiment of the invention is shown in which the image-developing device is separately provide on a substrate other than document bearing the designated print image-forming forming area. Form 200 is provided with microcapsular patch 202 and designated print image-forming forming area 204. No image-developing device is provided on form 200. In FIG. 14, document 206 is formed by coating the reactive adhesive composition on a release liner followed by lamination with a transparent film so that the laminate can be die-cut to form multiple, peelable image developing devices 208a, 208b, etc. After a print image is formed in the print image-forming area 204 as previously described, peelable image-developing device 208a can be removed from form 206 and applied to area 204 in the manner shown previously for area 84 in FIG. 10. FIG. 15 shows partial peeling of die-cut transparent film 210 along with the reactive pressure-sensitive adhesive 212 from release coating 214 of liner 216 for application of transparent film 210 to latent image in area 204 of FIG. 13. Although FIG. 14 shows the image developing devices as multiple, peelable patches on a sheet, it will be understood that each image-developing device 208a, 208b, 208c, etc. could be supplied as a separate patch having an attached, co-extensive, release liner, thereby providing the patch as a single unit to be later peeled and applied to a form, if desired.

The invention will be further illustrated by the following examples. It should be understood that the examples are not intended to limit the scope of this invention. Percentages are by weight unless otherwise indicated.

EXAMPLE 1

This example demonstrates use of the color developing device to develop a latent image print.

A slurry containing 100 grams (50 weight percent solids) of microcapsules having a particle diameter in the range of 15 to about 25 microns and containing the black color former, 2-anilino-3-methyl-6-dibutylaminofluoran, 10 grams of a 6 weight percent polyvinyl alcohol solution and 15 grams of starch particles was spot coated over an area of a one square inch rectangle on a security document.

A reactive pressure-sensitive adhesive was formed from a mixture of 200 grams of hot-melt, rubber-based adhesive, which is commercially available as MM 4144 from National Starch and Chemicals, 120 grams of zincated alkylphenol-formaldehyde novolak, which is commercially available as HRJ-2053 from Schenectady International, 80 grams of polybutene, which is commercially available as Indopol H-1900 from AMOCO Chemical Company, and 60 grams of Sure-Sol 290 oil from Koch Chemical Company.

The mixture was heated under a mild stirring until a homogenous phase was obtained. The resulting hot-melt liquid was coated on a release liner which was then laminated with a transparent polyethylene film. The assembly was cut into a size of a rectangle of about 1½ inch by 1½ inch.

Next, the non-release surface of the release liner was glued on a security document adjacent to a fingerprint receiving area. A designated fingertip was rubbed over the coating of the microcapsules to coat the fingertip with the black color former. The fingertip is then pressed on the designated fingerprint receiving area to form a latent fingerprint within the fingerprint receiving area.

The laminate of the transparent film and reactive pressure-sensitive adhesive was then peeled off the liner and the transparent film is placed over the latent fingerprint with the reactive adhesive in contact with the latent fingerprint. An instant black-colored fingerprint was developed, which was protected from marring and defacing by the transparent film.

EXAMPLE 2

This example demonstrates development of a visible image print without use of the image developing device.

A slurry containing 150 grams (50 weight percent solids) of microcapsules having a particle diameter of from about 15 to about 25 microns containing the red color former 3,3-bis(1-octyl-2-methylindol-3-yl)phthalide, 25 grams (65 weight percent solids) of melamine-formaldehyde condensate, 10 grams (6 weight percent) of polyvinyl alcohol solution and 25 grams of starch particles was coated on a security document as a spot of one inch by one inch square.

One hundred-eighty grams of a 3.5 weight percent polyvinyl alcohol solution, 90 grams of calcium carbonate, 58 grams of Dow Latex 620A and 5 grams of defoamer were added to 200 grams of a water-based dispersion of the color developer, zincated alkylphenol-formaldehyde novolak, commercially available as HRJ-10802 from Schenectady International.

The resulting mixture was coated within the area of a rectangle of about two square inches. By rubbing a designated finger over the microcapsule coating and imprinting it over the novolak color developer coating, an instant red-colored fingerprint was developed.

EXAMPLE 3

The procedure of Example 2 was repeated. A transparent plastic film with the reactive pressure-sensitive adhesive having the structure of the image developing device of Example 1 was placed over the visible, colored fingerprint of Example 2. A more intense red-colored fingerprint was obtained and the transparent plastic cover protected the fingerprint from staining.

Although the invention has been described with a certain degree of particularity, it is understood that the present disclosure has been made only by way of example and that numerous changes in the details of construction and the combination and arrangement of parts may be resorted to without departing from the spirit and scope of the invention. Thus, the scope of the invention should not be limited by the foregoing specification.

What is claimed is:

1. A method for forming fingerprints which comprises
providing a first substrate having a first surface bearing a designated print image-forming area,
said first substrate further bearing a localized coating of pressure-sensitive microcapsules containing a substantially colorless, image-forming reactant for forming an image of a print in said localized, image-forming area, said localized coating of said pressure-sensitive microcapsules being spaced apart from said designated print image-forming area, and
an image-developing device comprising a second substrate, said second substrate being substantially transparent and having a first surface and a second surface, said first surface of said second substrate being coated with a dual-functional, reactive adhesive composition comprising a pressure-sensitive adhesive and an image-forming co-reactant capable of reacting with said image-forming reactant to form a visible, colored image in said designated print image-forming area,
said second substrate being releasably attached to said first substrate and spaced apart from each of said designated print image-forming area and said localized coating of said pressure-sensitive microcapsules,
contacting a member to be printed with said pressure-rupturable microcapsules under sufficient pressure from said member to rupture said microcapsules and release said image-forming reactant on said member to be printed, applying said coated member to be printed onto said print image-forming area to transfer said image-forming reactant to said print image-forming area to form an image of the print of said member to be printed in said print-image forming area, and
separating said second substrate from said first substrate and adhering said second substrate to said first substrate with said reactive adhesive composition superposed and in direct contact with said print-image forming area.

2. The method of claim 1, wherein said image-forming reactant is a color former and said image-forming co-reactant is a color developer.

3. The method of claim 2, wherein transfer of said color former to said print image-forming area forms a latent image of said print of said member to be printed in said print-image forming area, and said latent image is converted to a visible colored image by application of said reactive adhesive comprising said color developer to said print image-forming area.

4. The method of claim 2, wherein said print-image forming area has been coated with a color developer and transfer of said color former to said print image-forming area forms a visible colored image of said print of said member to be printed in said print image-forming area.

5. A method for forming prints, which comprises
providing a first substrate having a first surface substantially fully coated with a color developer and having a designated print image-forming area, said designated print image-forming area being on said color developer coating,
said color developer coating bearing a localized coating of pressure-sensitive microcapsules containing a substantially colorless, color former, capable of reacting with said color developer to form a colored, visible image, said print-forming area and said localized coating of pressure-sensitive microcapsules being spaced apart,
contacting a designated member to be printed with said pressure-sensitive microcapsules under sufficient pressure from said designated member to rupture said microcapsules and release said color former on said member to be printed to form a coated member to be printed,
applying said coated member to be printed onto said print image-forming area and transferring said color former to said print image-forming area for reaction with said color developer to form a colored visible image of the print of said member to be printed in said print-image forming area.

6. The method of claim 5, wherein said localized coating of pressure sensitive microcapsules is in direct contact with said color developer coating.

7. The method of claim 5, wherein said localized coating of pressure sensitive microcapsules is separated from said color developer coating by an uncoated substrate.

8. A self-provided imprinting system for forming fingerprints comprising a first substrate having a first surface bearing a designated print image-forming area, said first substrate further bearing a localized coating of pressure-sensitive microcapsules containing a substantially colorless, image-forming reactant for forming an image of a print in said localized, print image-forming area, said localized coating of said pressure-sensitive microcapsules being spaced apart from said designated print image-forming area, and an image-developing device comprising a second substrate, said second substrate being substantially transparent and having a first surface and a second surface, said first surface of said second substrate being coated with a dual-functional, reactive adhesive composition comprising a pressure-sensitive adhesive and an image-forming co-reactant capable of reacting with said image-forming reactant to form a visible, colored image in said designated print image-forming area, said second substrate being releasably attached to said first substrate and spaced apart from each of said designated print image-forming area and said localized coating of said pressure-sensitive microcapsules.

9. The imprinting system of claim 8, wherein said image-forming reactant is a color former and said image-forming co-reactant is a color developer.

10. The imprinting system of claim 9, wherein said print image-forming area is free from co-reactant capable of reacting with said encapsulated reactant to form a visible image.

11. The imprinting system of claim 9, wherein said print image-forming area is coated with a co-reactant capable of reacting with said encapsulated reactant to form a visible image.

12. The imprinting system of claim 9, wherein said first surface of said first substrate is substantially fully coated with a co-reactant capable of reacting with said encapsulated reactant to form a visible image.

\* \* \* \* \*